United States Patent [19]
Wang et al.

[11] Patent Number: 5,686,305
[45] Date of Patent: Nov. 11, 1997

[54] ESTABLISHMENT OF NEW CELL LINES FROM *PSEUDALETIA UNIPUNCTA* WITH DIFFERENTIAL RESPONSES TO BACULOVIRUS

[75] Inventors: Ping Wang, Columbia, Md.; Robert R. Granados, Ithaca, N.Y.

[73] Assignee: Boyce Thompson Institute for Plant Research, Inc., Ithaca, N.Y.

[21] Appl. No.: 806,193

[22] Filed: Feb. 26, 1997

[51] Int. Cl.$^6$ .............................. C12N 5/00; C12N 5/06; C12N 5/16

[52] U.S. Cl. .................................................. 435/348

[58] Field of Search ................................. 435/348

[56] References Cited

PUBLICATIONS

Chejanovsky, N. and Gershburg, E. 1995. The wild-type *Autographa californica* nuclear polyhedrosis virus induces apoptosis of *Spodoptera littoralis* cells. Virology 209, 519–525.

Dwyer, K. G., Webb, S. E., Shelton, A. M. an////d Granados, R. R. 1988. Establishment of cell fines from *Pieris rapae* embryos: Characterization and susceptibility to baculoviruses. *J. Invertebr. Pathol.* 52, 268–274.

(List continued on next page.)

Primary Examiner—Sandra E. Saucier
Attorney, Agent, or Firm—Brown, Pinnisi & Michaels

[57] ABSTRACT

This disclosure presents the establishment of a new cell line from *Pseudaletia unipuncta* embryos. This cell line demonstrated the ability to produce high numbers of baculoviruses in cell culture. These virus particles are found internally in the cells in occlusion bodies. In the study of *Pseudaletia unipuncta* two baculoviruses were found to infect this species: *P. unipuncta* nuclear polyhedrosis virus (PuNPV), and *P. unipuncta* granulosis virus (PuGV). In addition, the cell line was also selected and cultured for its ability to grow in suspension while maintaining high levels of OB production.

7 Claims, 4 Drawing Sheets

Beta-Galactosidase Activity

OTHER PUBLICATIONS

Granados, R. R., Li, G., Derkson, A. C. G. and McKenna, K. A. 1994. A new cell line from *Trichoplusia ni* (BTI-Tn-5B 1-4) susceptible to *Trichoplusia ni* single enveloped nuclear polyhedrosis virus. *J. Invertebr. Pathol.*, 64, 260-266.

Harris, H.D. and Hopkinson, A. 1976. "Handbook of Enzyme Eletrophoresis in Human Genetics", North-Holland Publishing Co., Amsterdam.

Hink, W.F. and Strauss, E. 1976. Growth of the *Trichoplusia ni* (TN-368) cell line in suspension culture. hi "Invertebrate Tissue Culture, Applications in Medicine, biology, an Agriculture." (E. Kurstak and K. Maramorosch, Eds.), pp. 297-300. Academic Press, New York.

Martignoni,M.E. and Iwai, P. J. 1986. "A Catalog of Viral Diseases of Insects, Mites, and Ticks", 4th edn. Portland, Oregon: USDA Forest Service PNW-195.

Miltenburger. H. C., Naser, W. L. and Harvey, J. P. 1984. 'Me cellular substrate: A very important requirement for baculovirus in vitro replication'. Z Naturforsch., 39, 993-1002.

Tanada, Y. 1985. A synopsis of studies on the synergistic property of an insect baculovirus: A tribute to Edward A. Steinhaus. *J. Invertebr. Pathol 45*, 125-138.

Vanghn, J. L., Goodwin, R. H., Tompkins, G. J. and McCawley, P. 1977. The establishment of two cell lines from the insect *Spodoptera frugiperda* (Lepidoptera: noctuidae). In Vitro 13, 213-217.

Vaughn, J. L. 1994. Lepidopteran cell culture. In "Arthropod Cell Culture Systems," (K. Maramorosch and A. H. McIntosh, Eds.), pp.37-50. CRC Press, Boca Raton, FL.

Wang, P., Granados, R. R. and Shuler, M. L. 1992. Studies on serum-free culture of insect cells for virus propagation and recombinant protein production. *J. Invertebr. Pathol.* 59, 46-53.

Wang, P., Hammer, D. A. and Granados, R. R. 1994. Interaction of *Trichoplusia ni* granulosis virus-encoded enhancin with midgut epithelium and peritrophic membrane of four lepidopteran insects. *J. Gen. Virol.* 75, 1961-1967.

Wickham, T. J., Davis, T., Granados. R. R., Shuler, M. L. and Wood, H. A. 1992, Screening of insect cell lines for the production of recombinant proteins and infectious virus in the baculovirus expression system.*Biotechnol. Prog.* 8, 391-396.

Wickham, T. J. and Nemerow, G. R. 1993. Optimization of growth methods and recombinant protein production in BTI-Tn-5B1-4 insect cells using the baculovirus expression system. *Biotechnol Prog.* 9, 25-30.

Winstanley, D. and Crook, N. E. 1993. Replication of *Cydia pomonella* granulosis virus in cell cultures. *J. Gen. Virol.* 74, 1599-1609.

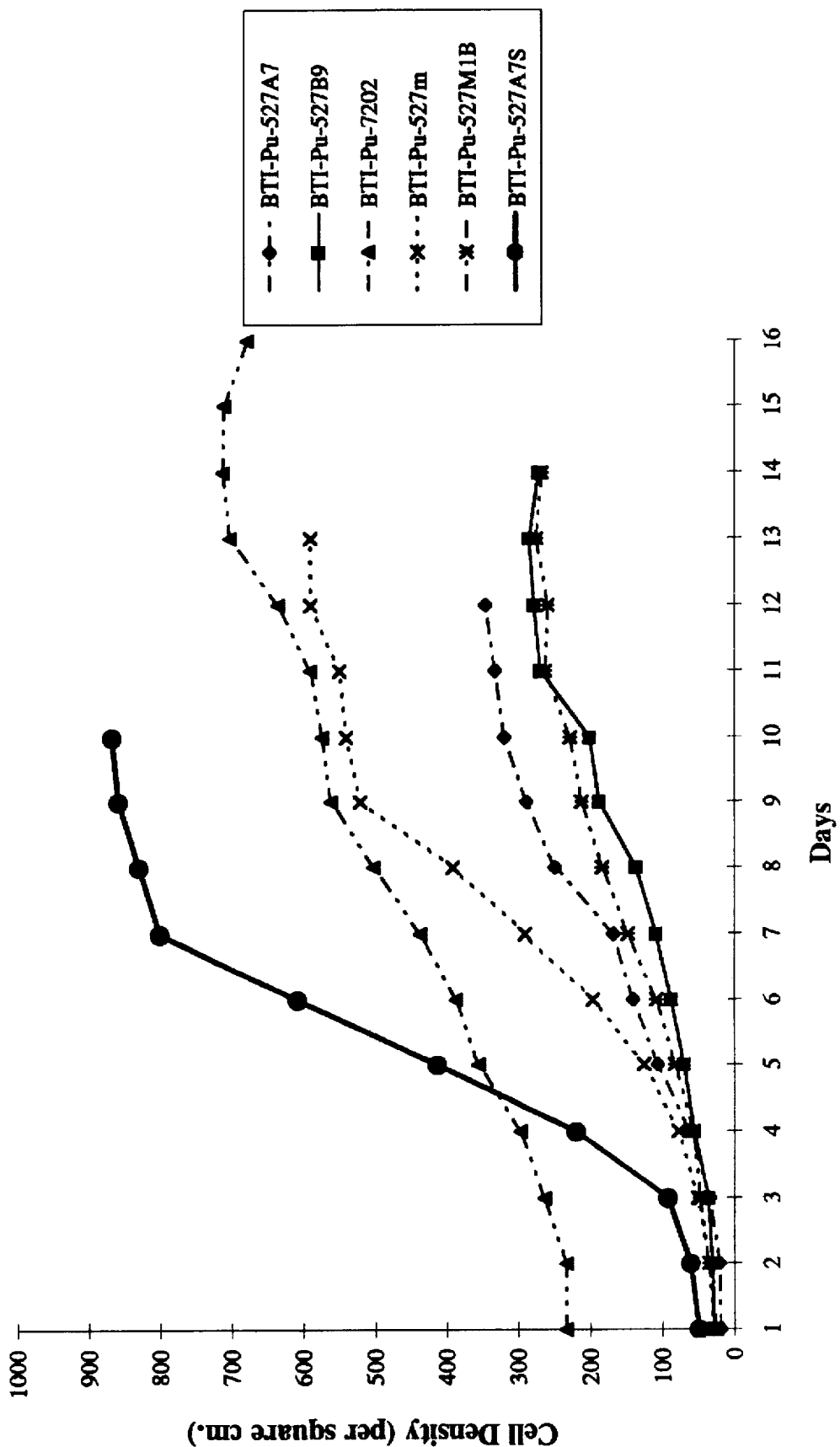
Figure 1. Cell Number Increase Over Time

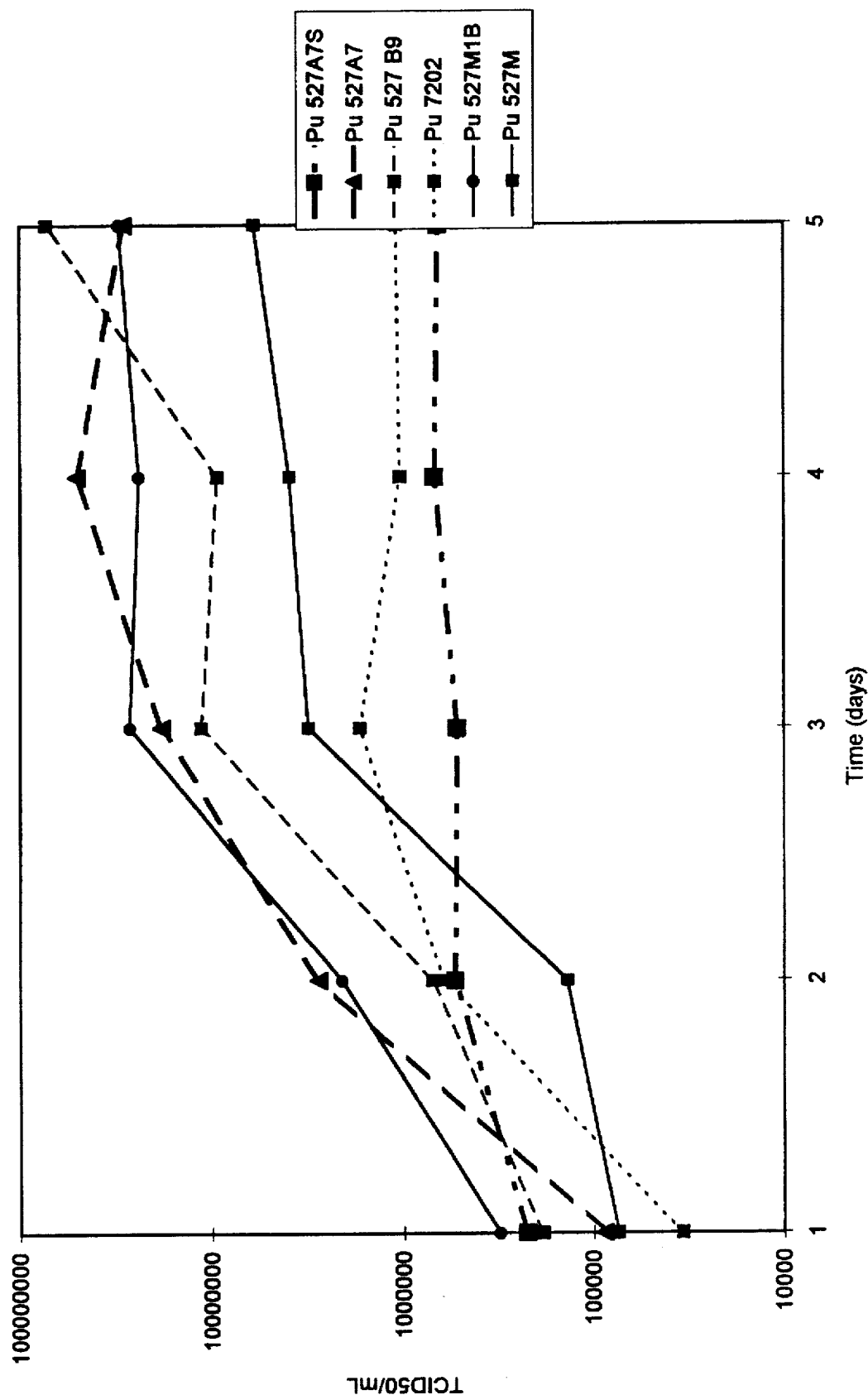
Figure 2. AcMNPV BV Titer

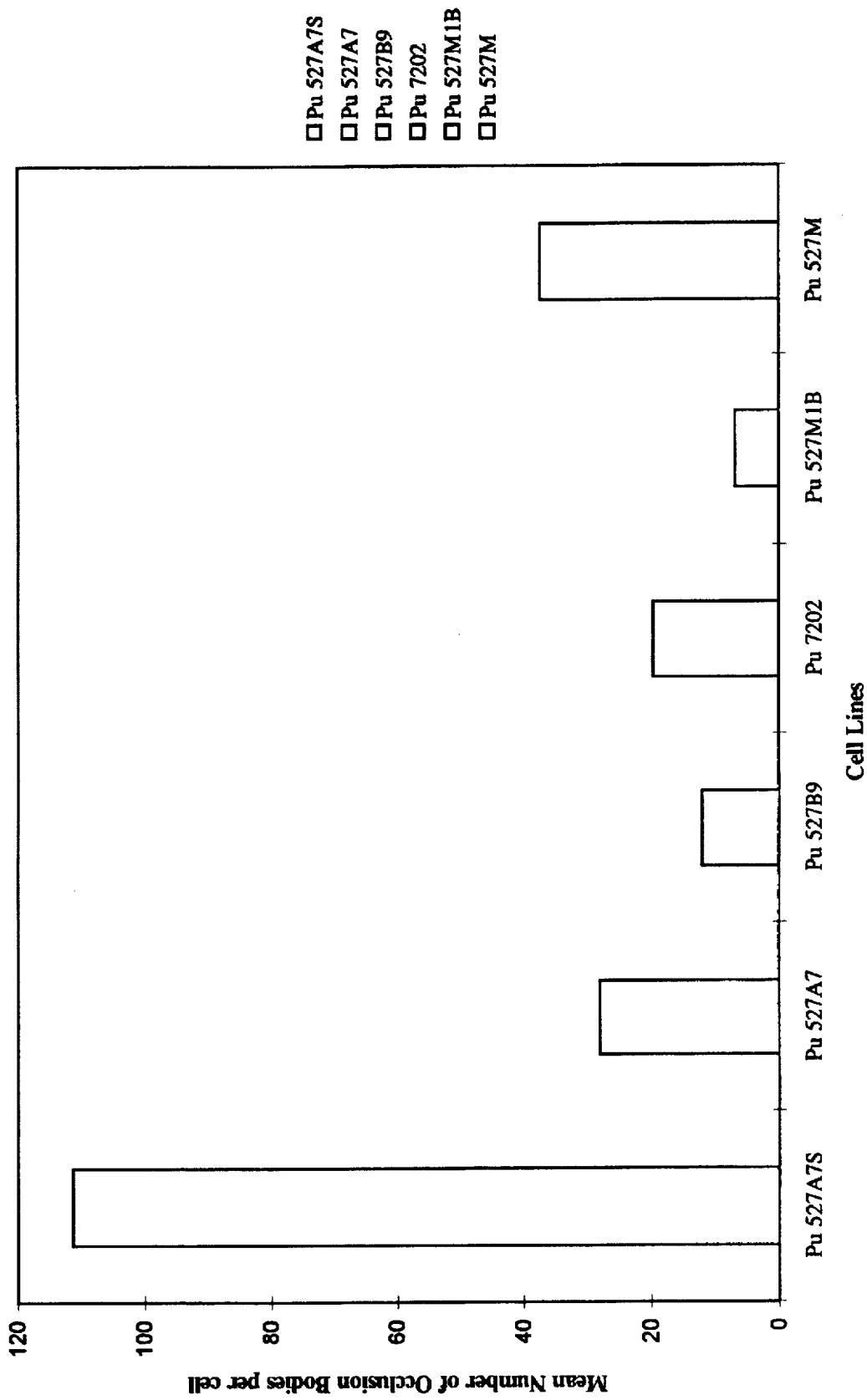

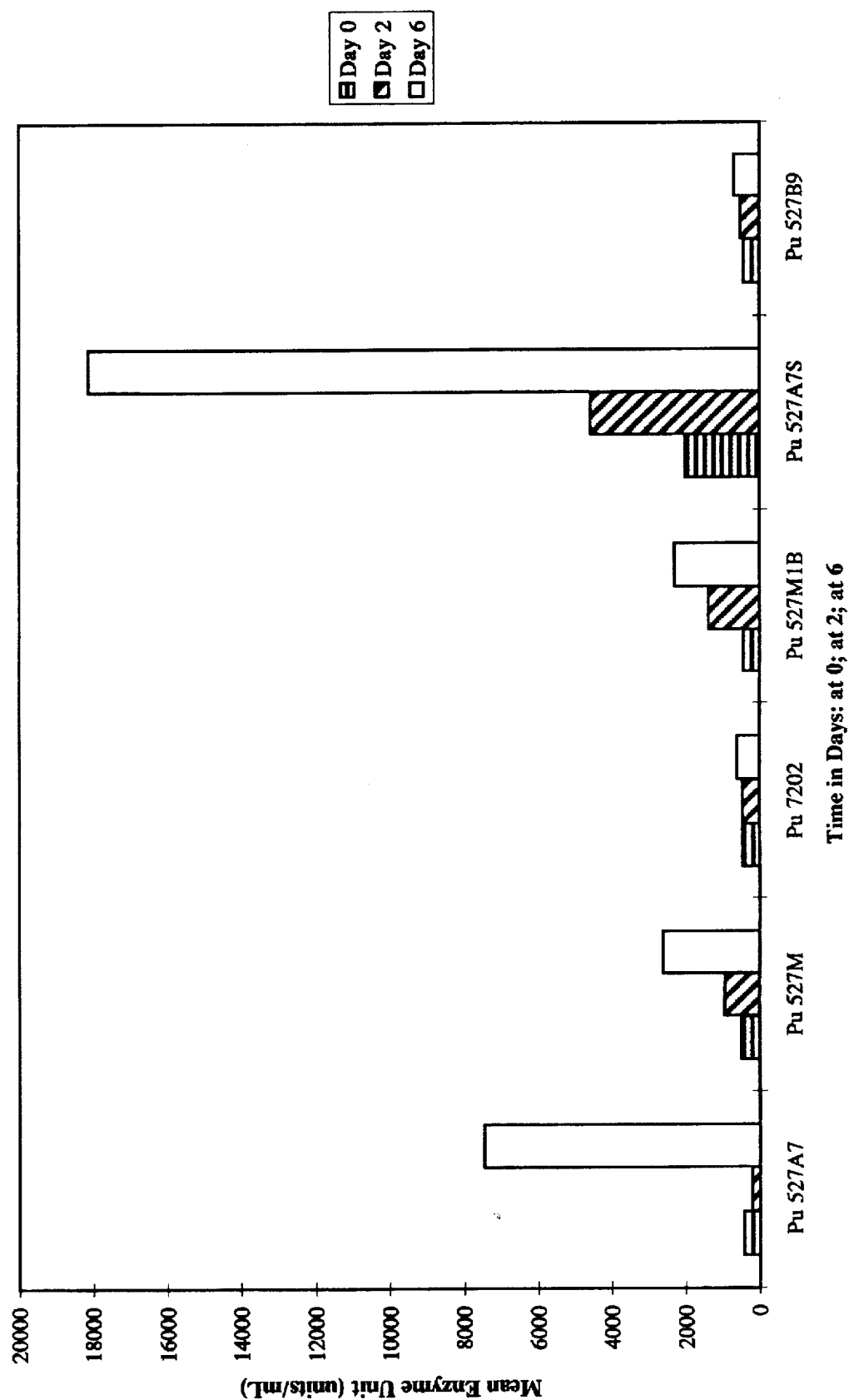

ESTABLISHMENT OF NEW CELL LINES FROM *PSEUDALETIA UNIPUNCTA* WITH DIFFERENTIAL RESPONSES TO BACULOVIRUS

FIELD OF THE INVENTION

The invention pertains to the development of a novel insect cell line. More particularly, the invention pertains to the creation of a *Pseudaletia unipuncta* cell line which produces large numbers of viral occlusion bodies, themselves containing large numbers of baculovirus particles.

BACKGROUND OF THE INVENTION

Since Grace (1962) established the first insect cell line, insect cell culture technology has been progressing at a rapid rate. Establishment of new insect cell lines gives those in both academia and commercial research the ability to use insect cell culture technology for various needs, such as for simple genetics research, the study of the susceptibility of insect cells to specific insect viruses (Winstanley and Crook, 1993; Granados et al., 1994, both incorporated herein by reference), use with already existing expression vectors for recombinant protein expression in various insect cell lines, and potentially to develop high production levels of insect viruses for use in pest control research (Wickham and Nemerow, 1993; Wickham et al., 1992, both articles incorporated herein by reference). To date, more than 150 insect cell lines have been developed from various Lepidopteran species since the first such insect cell line was established in the early 60's (Vaughn, 1994, incorporated herein by reference).

As suggested above, insect cell lines have been used successfully to produce recombinant proteins, and pharmaceuticals, in large part due to the development of a expression vector system. An expression vector system entails the use of a shuttle, such as a virus, plasmid, baculovirus, or other construct, to move designated and/or selected DNA into a given system such that expression of the transfer gene occurs. In the current application a baculovirus expression vector system or (BEVS), useful in the insertion of DNA into a given target cell or cell line, was used.

A baculovirus is an insect infecting virus, and the ability to use this gene shuttle allows the recombinant baculoviruses of the BEVS to insert selected DNA into an insect cell line amenable to interaction with a given expression vector system, such that expression of the specific protein so inserted is realized. This expression system utilizes the strong polyhedrin and p10 promoters present in the engineered vector system's genome (here the baculovirus genome) to produce large amounts of protein. To date, more than 200 foreign genes from viral, bacterial, invertebrate, mammalian and plant species have been expressed successfully in various insect cell lines with the BEVS. However, cell lines derived from different insect species often differ in their ability to produce virus particles or express recombinant proteins. Furthermore, culture conditions and media type often play major roles in selecting the appropriate cell line and system for a particular application or study.

With the ability to develop and maintain insect cell lines comes the ability to better understand and parse the cell biology of insects, and hence the improved ability to devise pest management strategies less reliant on the application of toxic chemical pesticides. Baculovirus research offers the possibility of engineering targeted baeuloviruses more capable of controlling or destroying specifically selected insect populations only. This creation of a precise and selective "biopesticide" would in essence eliminate the collateral effects to the natural environment that widespread chemical pesticide use is known to have caused. This is in addition to the creation of a weapon to use against insects that continue to develop relative immunities to all but the heaviest doses of conventional chemicals. Currently more than 600 various types of baculoviruses have been found (Martignoni and Iwai, 1986, incorporated herein by reference). However, the lack of insect cell lines engineered so as to be available for study is still a limiting factor in the study of most insect viruses. The lack of host cell lines for various granulosis viruses (GVs), a type of baculovirus, is an example of this limiting factor (Winstanley and Crook, 1993).

*Pseudaletia unipuncta* is an economically important agricultural pest, and is therefore of significant interest to those who seek to limit the damage caused by this insect. In the study of *Pseudaletia unipuncta*, two baculoviruses were found to infect this species: *P. unipuncta* nuclear polyhedrosis virus (PuNPV), and *P. unipuncta* granulosis virus (PuGV). It was in this latter species of virus that the baculovirus enhancing phenomenon, embodied by the activity of enhancin proteins which "enhanced" the infectivity of certain viruses, was initially discovered (Tanada, 1985 incorporated herein by reference). Another virus known to infect this insect is the *Autographa californica* multiple nuclear polyhedrosis virus (AcMNPV). Infection with this virus can also be increased with the presence of a baculovirus enhancin protein. (Wang et al., 1994, incorporated herein by reference).

As suggested above, research on the use of viruses as the active component in biopesticides relies primarily on the existence of insect cell lines with which to experiment and modify for the purpose. Unfortunately, until now there has not been a *P. unipuncta* cell line available to study the relationships amongst the viruses just mentioned and enhancins, or the use of these baculoviruses as tools through which to further develop biopesticides.

In this report, the establishment of cell lines from *P. unipuncta* embryos and the characterization of selected cell lines is presented. In addition, the susceptibilities of these cell lines to initiate AcMNPV infection, the ability of the newly derived cell line to produce high levels of baculovirus particles, and the apparent induction of apoptosis in some cells was examined.

SUMMARY OF THE INVENTION

An embryonic insect cell line from *Pseudaletia unipuncta* was established, characterized, and its susceptibility to *Autographa californica* multiple nuclear polyhedrosis virus (AcMNPV) infection was examined. This embryonic *P. unipuncta* cell line had distinct characteristics in morphology and growth. The cell line developed was found to be both highly susceptible to virus infection and superior for baculovirus production, producing over 100 AcMNPV occlusion bodies (OBs) per cell, well above previously known levels. This *P. unipuncta* cell line was designated BTI-Pu-527A7S (hereinafter referred to as "A7S") cell line. This *P. unipuncta* cell line could be distinguished from SF21 and BTI-Tn-5B1-4 cell lines by its isozyme markers.

The cell line described in the application as BTI-Pu-527A7S, or under the abbreviation "A7S" has been deposited and tested for viability at the American Type Culture Collection, 12301 Parklawn Drive, Rockville, Md. 20852 on Feb. 7, 1997, and assigned the accession number ATCC CRL-12285, and will be available to the public, irrevocably and without restriction upon issuance of the patent under the terms and conditions of the Budapest Treaty.

BRIEF DESCRIPTION OF THE DRAWINGS

FIG. 1 Shows growth characteristics of the various cell lines used in the experiments, indicated in density of cells. A7S demonstrates its capability to grow in higher densities than any of the other cell lines used in comparison. As measured in cells per/$cm^2$.

FIG. 2. Shows production of AcMNPV BV in *P. unipuncta* cell lines. This data is shown in Table II.

FIG. 3. Shows production of AcMNPV OBs in *P. unipuncta* cell lines. Numerals refer to the numbers of OBs from $10^6$ cells. This data is also shown in Table III FIG. 4. Shows comparison of B-galactosidase expression in cell cultures of *P. unipuncta* cell lines infected with a recombinant AcMNPV. The enzyme activity in these cell cultures were determined at 2 and 6 days post infection (p.i.). This data is also shown in Table IV.

DESCRIPTION OF THE PREFERRED EMBODIMENT

At present, the majority of studies involving the baculovirus expression vector system (BEVS) utilize established cell lines, such as SF-21, SF-9, Tn-368 and Tn-5B1-4. To evaluate the capacity of the new A7S *P. unipuncta* cell line for recombinant protein production, the A7S and other *P. unipuncta* cell lines were exposed to a recombinant AcMNPV virus for purposes of comparisons. This virus was designated E2-β-Gal, and as its name implies, carries the beta-galactosidase gene as a marker of its activity. E2-β-Gal tests were run, and overall growth characteristics were determined for all the cell lines used including A7S, and those cell lines used as comparisons. For these results see Table IV and FIG. 4. β-galactosidase production in the cell line A7S was tested, and found to produce more of this protein than the other *P. unipuncta* cell lines which it was compared to.

Materials and Methods

Primary Cell Culture and Maintenance

*P. unipuncta* primary embryonic cell cultures were established by the methods originally developed by Miltenburger et al., (1984) and modified by Dwyer et al., (1988). TNM-FH medium (Hink and Strauss, 1976) with 10% fetal bovine serum was used throughout the studies. Subculture was accomplished using Costar (Cambridge, Mass.) cell scrapers.

For these studies, the passage number of the cell lines ranged from 100 to 125 for BTI-Pu-527A7, 50 to 67 for BTI-Pu-527139, 42 to 58 for BTI-Pu-7202, 72 to 96 for BTI-Pu-527m and 47 to 64 for BTI-Pu527M I B. The A7S cells used in this study were between passages 4 to 10 after the suspension characteristics of the cell line were stabilized by repeated selection of suspended cells originally present in the BTI-Pu-527A7 cell line.

| Procedure for Establishment of New Embryonic Cell Lines |
|---|
| A. 300–400, 24-hour-old eggs are sterilized in 2% chlorox, 70% ethanol, and rinsed in GTC-100 tissue culture medium. |
| B. With a rubber policeman the eggs are crushed through a 100 mm sieve into fresh medium. |
| C. The homogenate is centrifuged at 200 g for 5 minutes and the pellet resuspended in 5 mL of TNM-FH tissue culture medium. |
| D. The cells are seeded into 25 $cm^2$ tissue culture flask and incubated at 28° C. |

Cell Size Measurement

Printed images of cells were obtained from individual cell lines using an Olympus inverted phase contrast microscope connected to a video printer. The cell sizes were measured from these prints and converted to actual size according to a calibrated magnification factor. Average cell dimensions were determined from 30 to 50 cells and 95 % confidence intervals for the means were calculated. See Table I.

Cell Growth Kinetics

Cells in log phase were suspended using cell scrapers and 5 mL of cell suspension was seeded into 25-$cm^2$ tissue culture flasks (Corning, N.Y.) at routine subculture densities. Cell densities for each flask were determined at 24-hour intervals by counting cells in five regions of each flask as described by Wang et al., (1992). The number of cells per 5 $cm^2$ was equivalent to the number of cells per mL.

Isozyme Analysis

Cells in log phase were harvested and washed with PBS by low speed centrifugation. The cells were resuspended in 0.0625 M Tris-HCl (pH 6.8), 10% glycerol and 0.002% bromophenol blue and disrupted by an initial freeze-and-thaw step followed by sonication. Cell debris was removed by centrifugation and the supernatants used for isozyme analyses. Two other cell lines, SF-21 (Vaughn et al., 1977) and BTI-Tn5 B 1-4 (Granados et al, 1994) (Commercial name High Five™, Invitrogen, San Diego, Calif.), along with 24 hour old *P. unipuncta* eggs, were included in isozyme analysis as references for the *P. unipuncta* cell lines. For isozyme analyses, cell extracts were separated by polyacrylamide gel electrophoresis with a 3 % stacking gel and a 7.5 % separation gel. The isozymes, lactate dehydrogenase and esterase, were detected using the methods of Harris and Hopkinson (1976).

Infection with AcMNPV

To test the susceptibility of each cell line to AcMNPV infection, log phase cells in 25-$cm^2$ flasks were inoculated with AcMNPV infectious medium at a multiplicity of infection (hereinafter referred to as the MOI) of 10 pfu (plaque forming units)/cell. The cells were incubated at 28° C. Cytopathology was observed using an inverted phase contrast microscope.

For the screening of novel cell lines for susceptibility to *Autographa californica* multiple nuclear polyhedrosis virus (AcMNPV) and expression of model recombinant viruses with the following procedures were used successfully.

1. New cell lines were subcultured in serum-containing medium for 15–20 passages in 25 $cm^2$ T-flasks prior to initial testing. During this time, cell cultures are selected for properties such as their ability to grow as anchorage-dependent or suspension cultures and short doubling time.
2. At this time (after about 30 passages) selected cell lines are adapted to serum-free media. Depending on the cell lines, adaptation to a serum-free medium could take an additional 5–20 passages.
3. Screening of cell lines for virus and/or recombinant protein production usually will occur at about passages 40–50. A similar method can be used for evaluating OB production in selected insect cell lines.

4. Cell lines can be further improved and stabilized if they are cloned. This step will require re-evaluation of the cloned cell lines to produce high levels of virus or recombinant proteins. Further characterization of the lines would include isozyme analysis, karyotyping, determining cell doubling times, and growth curve analysis.

All cell lines were established and maintained in TNM-FH medium in 25 cm$^2$ tissue culture flasks at 28° C. The Tn-5B1-4 and SF-21 cells were used as controls in some experiments (e.g. isozyme analysis).

Production of AcMNPV BV

Suspended log phase cells from each cell line were inoculated with AcMNPV as described above. Virus absorption was allowed to proceed at 28° C. for 1 hour. After inoculation, the cells were washed with fresh TNM-FH medium to remove unabsorbed virus and 5×10$^5$ cells in 0.5 mL medium was aliquoted into individual wells of a 24-well tissue culture plate (Corning, N.Y.) in triplicate. The media from three wells were collected at intervals of 24 hours. The infectious medium containing AcMNPV budded virus (BV) was titrated by the TC ID$_{50}$ serial dilution method using SF-21 cells, as previously described by Wang et al., (1992).

Production of AcMNPV Occlusion Bodies

Cells in log phase were inoculated with AcMNPV infectious medium at a MOI of 10 at 28° C. for 1 hour. The cells were then resuspended in fresh TNM-FH medium to a cell density of 5×10$^5$ cells/mL, aliquoted as two mL of the cell suspension into individual wells in a 6-well tissue culture plate (Corning, N.Y.), and incubated at 28° C. At 4 days post infection (p.i.), the cultures were collected and the cells disrupted by sonication to release virus occlusion bodies (OBs). OBs were isolated and washed with water several times by differential centrifugation. The number of OBs from each cell line were counted with a hemocytometer. The OB number in the A7S cell line exceeded 100 on a per cell basis average. BTI-Pu527A7 produced a moderate number of OBs, 28 per cell. The rest of the cell lines produced less than 1 OB on a per cell basis average. The cell line BTI-Pu-527M1B was at the low extreme, which produced only 7 OBs per 100 cells (FIG. 3).

Beta-Galactosidase Production

To examine virus infection and expression of B-galactosidase, cells were infected with a recombinant AcMNPV (AcMNPV 246) at a MOI of 10. The infection procedures were the same as those described above for AcMNPV BV production. Infected cultures were harvested at 0, 2 and 6 days post infection and kept at −70° C. For determination of B-galactosidase activity, harvested cell suspensions were disrupted by sonication and the supernatants used for enzyme assays. The enzyme assay procedure and the definition and calculation of activity units were as previously described. (Wang et al., 1992).

Results

Establishment of Cell Lines

In total, 89 cell lines were obtained from *P. unipuncta* embryos. After preliminary examination of cell morphology, growth characteristics and susceptibility to virus infection, a cell line was selected for further study and the remaining cell lines were frozen in liquid nitrogen or used for purposes of comparison. Of these A7S was superior in terms of OB and its ability to grow in suspension.

These cell lines were designated BTI-Pu-527A7, A7S, BTI-Pu-527139, BTI-Pu-527m, BTI-Pu-527M1B and BTI-Pu7202. Cell lines BTI-Pu-527A7, BTI-Pu527139 and BTI-Pu-7202 appeared to have a mixed cell morphology. Cell line changes in vital susceptibility during prolonged subculturing followed one of several paths. See the discussion of this below.

Cell lines BTI-Pu-527m, BTI-Pu-527M1B and A7S are mostly spherical in shape. Average sizes and other characteristics of some of these cell lines are summarized in Table I. The BTI-Pu-527m cells were the smallest, with an average diameter of 10.4 μM and A7S cells were the largest with a diameter of 18.5 μM. BTI-Pu-527A7 cells were mostly attached, with some cells tending to float in the medium. A7S is a suspension cell line developed by repeatedly selecting suspended cells for passage from the BTI-Pu-527A7 cell line, which normally grows attached to the surface of its culturing flask and/or plate. The rest of the cell lines are all attached.

TABLE I

Morphological and Growth Characteristics of *P. unipuncta* cell lines

| Cell Line | Size μM, Average ± S.E. | | Population Doubling Time (hours) | Density at stationary (cells/cm$^2$) |
|---|---|---|---|---|
| | Spherical Shape | Spindle Shape | | |
| BTI-Pu-527A7 | 14.9 ± 2.8 | (30.1 ± 7.4) × (9.6 ± 2.9) | 24 | 6.0 ± 0.2 × 10$^5$ |
| BTI-Pu-527B9 | 13.1 ± 2.5 | (41.6 ± 8.0) × (10.2 ± 2.6) | 38 | 5.1 ± 0.6 × 10$^5$ |
| BTI-Pu-7202 | 13.2 ± 2.7 | (40.8 ± 8.7) × (10.4 ± 2.3) | 104 | 3.0 ± 0.2 × 10$^5$ |
| ETI-Pu-527m | 10.4 ± 1.9 | | 35 | 10.3 ± 0.5 × 10$^5$ |
| BTI-Pu-527M1B | 12.6 ± 2.1 | | 60 | 4.4 ± 0.6 × 10$^5$ |
| BTI-Pu-527A7S | 18.5 ± 2.3 | | 21 | 3.7 ± 0.4 × 10$^5$ |

Cell Growth Kinetics

Duplicate growth kinetic determinations were performed for all 6 cell lines. No significant differences were observed between replicates. Therefore, only one set of data for each cell line is presented here.

Both cell growth rates and cell densities at stationary phases varied greatly among the *P. unipuncta* cell lines (see FIG. 1 and Table 1). The A7S cell line had the shortest cell population doubling time, at 21 hours. BTI-Pu-7202 cells had the longest population doubling time, 104 hours approximately. The cell line BTI-Pu-527m, with a moderate population doubling time (35 hours), reached a density of 10.3×10$^5$ cells/cm$^2$, which is equivalent to 5.2×10$^6$ cells/mL. The slowest growing cell line, BTI-Pu7202, only reached a density of 3.0×105 cells/cm$^2$, or the equivalent, 1.5×10$^6$ cells/mL.

Characteristic Isozyme Analysis

Analyses of the isozymes lactate dehydrogenase (LDH) and esterase (ES) from cell extracts showed that the established *P. unipuncta* cell lines were distinctively different from the two most commonly used insect cell lines, BTI-Tn-5B 1-4 and SF-21. The pattern of LDH did not show a distinguishable difference among the *P. unipuncta* cell lines. However, the esterase pattern showed significant differences among these cell lines.

BV liters tended to differ from each other, the AcMNPV BV titers did not correlate with OB formation in these cell lines. For example, BTI-Pu-527M1B rarely contained OBs, but it did produce BV at a level comparable to that from BTI-Pu-527A7 which displayed normal OB formation. In contrast, A7S produced a large number of OBs, but produced BV at a very low level. The production of BV in BTI-Pu-527m and BTI-Pu-7202, appeared to be low.

TABLE II

Production of AcMNPV BV in *P. unipuncta* cell lines
Production of AcMNPV BV Titers

| Cell Lines | Day 0 Titer Meas. | Day 1 Titer Meas. | Day 2 Titer Meas. | Day 3 Titer Meas. | Day 4 Titer Meas. |
|---|---|---|---|---|---|
| Pu 527A7S | $2.22 \times 10^6 \pm .74 \times 10^6$ | $5.33 \times 10^6 \pm .74 \times 10^6$ | $5.20 \times 10^6 \pm .71 \times 10^6$ | $6.87 \times 10^6 \pm 1.10 \times 10^6$ | $6.57 \times 10^6 \pm 1.39 \times 10^6$ |
| Pu 527A7 | $.87 \times 10^6 \pm .24 \times 10^6$ | $27.70 \times 10^6 \pm 1.50 \times 10^6$ | $183 \times 10^6 \pm 102 \times 10^6$ | $506 \pm 10^6 \pm 83.8 \times 10^6$ | $288 \times 10^6 \pm 60.30 \times 10^6$ |
| Pu 527 B9 | $1.85 \times 10^6 \pm .82 \times 10^6$ | $7.03 \times 10^7 \pm .89 \times 10^6$ | $114 \times 10^6 \pm 20.8 \times 10^6$ | $93.6 \times 10^6 \pm 10.40 \times 10^6$ | $732 \times 10^6 \pm 467 \times 10^6$ |
| Pu 7202 | $.34 \times 10^6 \pm .14 \times 10^6$ | $6.12 \times 10^6 \pm 1.47 \times 10^6$ | $16.8 \times 10^6 \pm 6.65 \times 10^6$ | $10.4 \times 10^6 \pm 1.80 \times 10^6$ | $10.80 \times 10^6 \pm 1.45 \times 10^6$ |
| Pu 527M1B | $3.11 \times 10^6 \pm .42 \times 10^6$ | $20.90 \times 10^6 \pm 9.08 \times 10^6$ | $268 \times 10^6 \pm 65.30 \times 10^6$ | $239 \times 10^6 \pm 121 \times 10^6$ | $306 \times 10^6 \pm 80.80 \times 10$ |
| Pu 527m | $.74 \times 10^6 \pm .15 \times 10^6$ | $1.38 \times 10^6 \pm .15 \times 10^6$ | $31.4 \times 10^6 \pm 11.50 \times 10^6$ | $39.5 \times 10^6 \pm 11.4 \times 10^6$ | $60.10 \times 10^6 \pm 3.17 \times 10^6$ |

TABLE III

Production of AcMNPV OBs in *P. unipuncta* cell lines
OB Production per cell

| Cell Line | Experiment Repetitions | Mean Number of OBs per Cell | Median | TRMEAN | STDEV | SEMEAN |
|---|---|---|---|---|---|---|
| Pu 527A7S* | 3 | 111.33 | 114.00 | 111.33 | 8.33 | 4.81 |
| Pu 527A7* | 3 | 28.00 | 26.00 | 28.00 | 7.21 | 4.16 |
| Pu 527B9 | 3 | 12.00 | 12.00 | 12.00 | 4.00 | 2.31 |
| Pu 7202 | 3 | 19.67 | 24.00 | 19.67 | 13.05 | 7.54 |
| Pu 527M1B | 3 | 7.00 | 8.00 *p1501X | 7.00 | 2.65 | 1.53 |
| Pu 527m | 3 | 37.33 | 32.00 | 37.33 | 9.24 | 5.33 |

*A7S and A7 cell lines were diluted 100 fold before OB production per cell was counted Susceptibility to AcMNPV When infected with AcMNPV, the *P. unipuncta* cell lines displayed very different cytopathogenic effects (CPE) from each other. BTI-Pu-527A7 and A7S showed typical CPE after AcMNPV infection, such as enlarged nuclei with a large number of OBs formed in the nuclei at late stages of infection. BTIPu-527m showed enlarged nuclei following infection, but only a small number of OBs formed in a few cells. Interestingly, when infected with AcMNPV, the cell lines BTI-Pu-527139, BTI-Pu-7202 and BTI-Pu-527M1B displayed cytolysis with fragmented nuclei and enlarged cells. Visualized microscopically, the cells eventually became vesicles containing lysed materials with small broken nuclei. OBs in these three cell lines were rare.

Production of AcMNPV BV

Production of AcMNPV BV in *P. unipuncta* cell lines is shown in both FIG. 2 and Table II. Although the AcMNPV Production of AcMNPV OBs Similar to the cytopathological observation noted above, the number of OBs produced in these *P. unipuncta* cell lines varied greatly. The A7S cell line was the highest AcMNPV OB producer. See FIG. 3.

Beta-Galactosidase Production

To examine whether the *P. unipuncta* cell lines could support AcMNPV replication throughout early to late stages, the expression of Beta-galactosidase, controlled by the late expression promoter (e.g. the polyhedrin promoter), was assayed by measuring Beta-galactosidase activity produced by the cells following infection with the recombinant virus, AcMNPV 246. Levels of expression of Beta-galactosidase in different cell lines were greatly different from each other (Table IV. and FIG. 4). The relative amounts of Beta-galactosidase expression in these cells were similar to that observed in OB production. A7S cells showed the highest expression level of the cell lines tested. BTI-Pu-527139 and BTI-Pu-7202 cells expressed the lowest levels among the cell lines.

TABLE IV

Beta-Galactosidase Activity
Mean Enzyme Unit/mL

| Cell Lines | Day 0 Data | Standard Error | Day 2 Data | Standard Error | Day 6 Data | Standard Error |
|---|---|---|---|---|---|---|
| Pu 527A7 | 433.6 | 11.5 | 204.2 | 75.5 | 7463.0 | 393.0 |
| Pu 527m | 488.4 | 52.5 | 939.7 | 52.1 | 2616.0 | 64.2 |
| Pu 7202 | 466.3 | 33.8 | 451.4 | 9.8 | 603.1 | 24.3 |
| Pu 527M1B | 436.6 | 7.4 | 1395.0 | 109.0 | 2305.0 | 212.0 |
| Pu 527A7S | 207.2 | 26.7 | 4573 | 722.0 | 18123.0 | 702.0 |
| Pu 527B9 | 429.2 | 13.3 | 514.3 | 46.4 | 684.5 | 3.7 |

In this study, *P. unipuncta* cell lines were established for the first time. Several of the original 89 established cell lines were characterized. Although the cell lines were derived from the same embryonic tissue source, these cell lines displayed different characteristics from each other. Analysis of the isozymes lactate dehydrogenase (LDH) from cell extracts did not show a distinguishable difference among the *P. unipuncta* cell lines. However, analysis of the isozymes lactate esterase (ES) from cell extracts was successful in demonstrating that the established *P. unipuncta* cell lines were distinctively different from the two most commonly used insect cell lines, BTI-Tn-5B 1-4 and SF-21.

At early stages (less than 10 passages), all the *P. unipuncta* cell lines were susceptible to AcMNPV infection with a large divergence in the numbers of AcMNPV occlusion bodies produced. However, after continuous subculturing, some cell lines have changed somewhat in their viral susceptibilities. According to the response of the cell lines to AcMNPV infection, the selected *P. unipuncta* cell lines could be categorized into three groups:

Group 1 was highly susceptible to AcMNPV infection and supported significant OB production. Cell lines in this group include BTI-Pu-527A7 and A7S.

Group 2 displayed cytolysis upon infection; however, these cells did support BV production. This group includes BTI-Pu-527B9, BTI-Pu-7202 and BTI-Pu-527M1B.

Group 3 consists of BTI-Pu-527m, which barely supported OB production; however, no cell lysis occurred as with group 2.

Group 1 cells showed typical CPE after AcMNPV infection with enlarged nuclei and, at the late stage, their nuclei were full of AcMNPV OBs (See the set of data comprising Table II.). Noticeably, the A7S cell line produced a significantly larger number of OBs, reaching over 100 OBs per cell on average, see FIG. 3. This cell line was found to be superior for virus production. Group 2 cell lines responded to AcMNPV infection by initiating apoptotic cell lysis. Upon infection, the cells started to swell, their nuclei became fragmented and eventually the cells turned into vesicles containing cell debris, thereby displaying the apoptotic pathway. However, the production of BV in this group appeared to be normal or only 10 fold lower than Group 1 cells. This suggested that AcMNPV replication in the early phase was not significantly affected even though the apoptosis pathway may have been already initiated. This is true though it appears that viral replication could not proceed into the late phase (i.e. OB production), (see Table II, and FIG. 3).

The extremely low expression level of B-galactosidase, which represents late viral gene expression, in these cell lines (FIG. 4) confirms that late gene expression in these cells is very limited, see also Table V, below. BTI-Pu-527m, differed from other cell lines in CPE from AcMNPV infection as well. Once infected with AcMNPV, the BTI-Pu-527m cells showed enlarged nuclei, but barely produced OBs and did not appear to lyse.

The morphological observations of AcMNPV infection in Group 2 cells described above suggests that the response of the cells to AcMNPV infection is apoptotic. In other words, AcMNPV exposure appears to induce apoptosis in these three *P. unipuncta* cell lines. Similar results have been observed in infection studies of *Pieris rapae* and *Spodoptera littoralis* cells with AcMNPV exposure (Dwyer et al., 1988; Chejanovsky and Gershburg, 1995, both incorporated herein by reference). *P. unipuncta* larvae are susceptible to AcMNPV infection (Wang et al., 1994, incorporated herein by reference), and it is known that AcMNPV encodes an apoptotic suppressor. However, the mechanism of apoptosis in the *P. unipuncta* cells induced by infection, and specifically by AcMNPV, have yet to be determined.

The *P. unipuncta* cell lines established, including A7S, were from the same embryonic tissue source, and have a closely related genetic background and similar cell physiology. However, on a cell line by cell line basis they display distinctly different responses to AcMNPV infection, as has been observed and recorded herein. These observation serve to underscore the point that the A7S cell line is an ideal candidate to be a host cell system in the study of specific interactions between the prototype baculovirus, AcMNPV, and insect cells, as well as in the commercial usage of the ability to produce so many occlusion bodies (and virion particles). In addition, the A7S cell line is a suspension cell line that produces over 100 AcMNPV OBs per cell in a stationary flask, demonstrating its superior productivity, and ease of use in the commercial context. As optimized for growth and infection this cell line is adapted to culturing in suspension culture at high cell densities, and carries with it the potential to produce significantly higher yields of AcMNPV OBs or other recombinant proteins than have been produced previously.

Literature Cited and Incorporated by Reference:

1. Chejanovsky, N. and Gershburg, E., *The wild-type Autographa Californica nuclear polyhedrosis virus induces apoptosis of Spodoptera littoralis cells*, Virology 209, 519–525 (1995).
2. Dwyer, K. G., Webb, S. E., Shelton, A. M. and Granados, R. R., *Establishment of cell lines from Pieris rapae embryos: Characterization and susceptibility to baculoviruses*, J. Invertebr. Pathol. 52, 268–274 (1988).
3. Granados, R. R., Li, G., Derksen, A. C. G. and McKenna, K. A., *A new cell line from Trichophusia ni (BTI-Tn-5B 1-4) susceptible to Trichoplusia ni single enveloped nuclear polyhedrosis virus*, J. Invertebr. Pathol., 64, 260–266 (1994).
4. Harris, H. D. and Hopkinson, A., *Handbook of Enzyme Electrophoresis in Human Genetics*, North-Holland Publishing Co., (Amsterdam 1976).
5. Hink, W. F. and Strauss, E., *Growth of the Trichoplusia ni (TN368) cell line in suspension culture*, In *Invertebrate Tissue Culture, Applications in Medicine, biology, and Agriculture*. (E. Kurstak and K. Maramorosch, Eds.), pp. 297–300. (Academic Press, New York 1976).

6. Martignoni, M. E. and Iwai, P. J. 1986. *A Catalog of Viral Diseases of Insects, Mites, and Ticks, In USDA Forest Service PNW*-195 (4th ed. Portland, Oreg. 1986).

7. Miltenburger, H. C., Naser, W. L. and Harvey, J. P., *The cellular substrate: A very important requirement for baculovirus in vitro replication,* Z. Naturforsch., 399 993–1002 (1984).

8. Mitsuhashi, J., *Invertebrate Cell System Applications,* Vol. 1 and 2 (CRC Press, Boca Raton, Fla. 1989).

9. Shuler, M. L., Wood, H. A., Granados, R. R. and Hammer, D. A. *Baculovirus Expression Systems and Biopesticides.* (Wiley-Liss, New York 1994).

10. Tanada, Y., *A synopsis of studies on the synergistic property of an insect baculovirus: A tribute to Edward A. Steinhaus,* J. Invertebr. Pathol. 45, 125–138 (1985).

11. Vaughn, J. L., Goodwin, R. H., Tompkins, G. J. and McCawley, P., *The establishment of two cell lines from the insect Spodoptera frugiperda (Lepidoptera: noctuidae),* In Vitro 13, 213–17 (1994).

12. *Lepidopteran cell culture, In, Arthropod Cell Culture Systems,* pp. 37–50 (K. Mararnorosch and A. H. McIntosh, Eds. 1977).

13. Wang, P., Granados, R. R. and Shuler, M. L., *Studies on serumfree culture of insect cells for virus propagation and recombinant protein production,* J. Invertebr. Pathol. 59, 46–53 (1992).

14. Wang, P., Hammer, D. A. and Granados, R. R., *Interaction of Trichophisia ni granulosis virus-encoded enhancin with midgut epithelium and peritrophic membrane of four lepidopteran insects,* J. Gen. Virol. 75, 1961–1967 (1994).

15. Wickham, T. J., Davis, T., Granados, R. R., Shuler, M. L. and Wood, H., *Screening of insect cell lines for the production of recombinant proteins and Infectious Virus in the baculovirus expression system,* Biotechnol. Prog. 8, 391–396 (1992).

16. Wickham, T. I. and Nemerow, G. R., *Optimization of growth methods and recombinant protein production in BTI-Tn-5B1-4 insect cells using the baculovirus expression system,* Biotechnol. Prog. 9, 25–30 (1993).

17. Winstanley, D. and Crook, N. E., *Replication of Cydia poinonella granulosis virus in cell cultures.,* J. Gem Virol. 74, 1599–1609 (1993).

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications and changes.

What is claimed is:

1. An insect cell line established from embryonic egg cells from an insect from the order Lepidoptera which is designated BTI-Pu-527A7S and has been deposited under the accession number ATCC CRL 12285 and has the following characteristics:

a) supports replication of virus, b) supports expression of protein after infection by a recombinant virus in a serum containing medium, c) can grow in suspension and/or shaker flask cell cultures; and d) grows in said serum containing medium and retains said ability to support replication of virus and to support expression of protein.

2. The insect cell line of claim 1 wherein at least 30 occlusion bodies are produced per cell line after infection by *Autographa californica* multiple nuclear polyhedrosis virus by the following steps:

a) seeding said cell line in at least one well at a density of $1 \times 10^5$ cells/mL in TNM-FH medium;

b) allowing said cells to attach for two to three hours;

c) drawing off the old medium;

d) adding 0.5 mL of fresh TNM-FH medium containing said virus at a multiplicity of infection of five;

e) measuring said occlusion body production at six days post infection.

3. The insect cell line of claim 2 wherein at least 100 occlusion bodies are produced per cell line after infection by *Autographa californica* multiple nuclear polyhedrosis virus.

4. The insect cell line of claim 2 wherein at least 90 occlusion bodies are produced per cell line after infection by *Autographa californica* multiple nuclear polyhedrosis virus.

5. The insect cell line of claim 1 wherein at least 10,000 mean units (Unit/mL) of expressed Beta-galactosidase is produced after infection by a recombinant *Autographa californica* multiple nuclear polyhedrosis virus by the following steps:

a) seeding said cell line in at least one well at a density of $1 \times 10^5$ cells/mL;

b) allowing said cells to attach for two to three hours;

c) drawing off the old medium;

d) adding 0.5 mL of fresh medium contain said recombinant virus at a multiplicity of infection of ten;

e) centrifuging said combination of cells, medium and virus at 1,000×g for 1 hour;

f) removing said media from said centrifuged combination; and g) adding 0.5 mL of fresh medium;

h) measuring said Beta-galactosidase production at six days post infection.

6. An insect cell line with all of the identifying characteristics of the cell line identified as BTI-Pu-527A7S and deposited under the accession number ATCC CRL 12285.

7. An insect cell line established from the embryonic egg cells of the insect *Pseudaletia unipuncta*, from the order Lepidoptera, which is designated BTI-Pu-527A75 having all of the identifying characteristics of the insect cell line.

* * * * *